(12) United States Patent
Willardsen et al.

(10) Patent No.: US 11,013,243 B2
(45) Date of Patent: May 25, 2021

(54) CANOLA PROTEIN PRODUCT WITH LOW PHYTIC ACID CONTENT ("C702")

(76) Inventors: Randy Willardsen, Roseville, CA (US); Martin Schweizer, Winnipeg (CA); Kevin I. Segall, Winnipeg (CA)

( * ) Notice: Subject to any disclaimer, the term of this patent is extended or adjusted under 35 U.S.C. 154(b) by 0 days.

(21) Appl. No.: 13/532,878

(22) Filed: Jun. 26, 2012

(65) Prior Publication Data

US 2013/0005946 A1 Jan. 3, 2013

Related U.S. Application Data

(60) Provisional application No. 61/457,887, filed on Jun. 29, 2011.

(51) Int. Cl.
| | | |
|---|---|---|
| *C07K 14/415* | (2006.01) | |
| *A23J 1/14* | (2006.01) | |
| *A23J 3/14* | (2006.01) | |
| *A23L 33/185* | (2016.01) | |
| *C07K 1/36* | (2006.01) | |

(52) U.S. Cl.
CPC . *A23J 1/14* (2013.01); *A23J 3/14* (2013.01); *A23L 33/185* (2016.08); *C07K 1/36* (2013.01); *C07K 14/415* (2013.01)

(58) Field of Classification Search
CPC .. A23J 1/14; A23J 3/14; A23L 33/185; C07K 1/36; C07K 14/415
USPC ............... 426/589, 656; 530/377, 378
See application file for complete search history.

(56) References Cited

U.S. PATENT DOCUMENTS

| | | | |
|---|---|---|---|
| 4,889,921 A | | 12/1989 | Diosady et al. |
| 5,844,086 A | * | 12/1998 | Murray ............... A23J 1/14 530/377 |
| 6,005,076 A | | 12/1999 | Murray |
| 2003/0060607 A1 | * | 3/2003 | Diosady et al. ............ 530/418 |
| 2005/0255226 A1 | * | 11/2005 | Schweizer ............ A23J 1/14 426/656 |
| 2009/0318671 A1 | * | 12/2009 | Schweizer ........... C07K 14/415 530/377 |
| 2010/0010198 A1 | * | 1/2010 | Schweizer et al. .......... 530/377 |

FOREIGN PATENT DOCUMENTS

| | | |
|---|---|---|
| CA | 2661397 | 2/2008 |
| CA | 2728441 | 1/2010 |
| WO | WO2004/112493 | 12/2004 |
| WO | WO2005/107492 | 11/2005 |
| WO | WO2010/020039 | 2/2010 |

* cited by examiner

*Primary Examiner* — Erik Kashnikow
*Assistant Examiner* — Bhaskar Mukhopadhyay

(57) ABSTRACT

Canola protein products having a protein content of at least about 60 wt % (N×6.25) d.b., preferably at least about 90 wt %, more preferably at lease about 100 wt %, and low phytic acid content, are produced by extracting canola seeds or canola oil seed meal with an aqueous calcium salt solution, preferably calcium chloride solution, to cause solubilization of canola protein from the seeds or meal.

28 Claims, No Drawings

US 11,013,243 B2

CANOLA PROTEIN PRODUCT WITH LOW PHYTIC ACID CONTENT ("C702")

FIELD OF INVENTION

This invention relates to the production of a canola protein product.

BACKGROUND TO THE INVENTION

Canola oil seeds and canola oil seed meal resulting from the recovery of canola oil from canola seeds typically contain anti-nutritional factors. The present invention is concerned with a procedure for processing canola seeds or canola oil seed meal to prepare a canola protein product having a low content of anti-nutritional factors, particularly phytic acid. Such a product would be valuable for various nutritional applications, including as an ingredient in milk replacers for animal nutrition.

SUMMARY OF INVENTION

In accordance with one aspect of the present invention, there is provided a method of preparing a canola protein product having a protein content of at least about 60 wt % (N×625) dry weight basis (d.b.), preferably at least about 90 wt % and more preferably at least about 100 wt %, which comprises:
 (a) extracting canola seeds or canola oil seed meal using an aqueous calcium salt solution to cause solubilisation of canola protein from the seeds or meal and to provide an aqueous canola protein solution,
 (b) separating the aqueous canola protein solution from spent canola oil seed meal or residual seed material and oil if the extraction was done on canola seeds,
 (c) optionally concentrating the separated aqueous canola protein solution,
 (d) optionally diafiltering the concentrated canola protein solution, and
 (e) optionally drying the concentrated and diafiltered canola protein solution.

The resulting product has a low phytic acid content, generally less than about 1.5 wt %, preferably less than about 0.5 wt %, and a high nutritional value.

GENERAL DESCRIPTION OF INVENTION

The initial step of the process of providing the canola protein product involves solubilizing proteinaceous material from canola oil seeds or canola oil seed meal. When canola oil seeds are utilized as the protein source, the seeds may be ground to provide a ground mass of canola oil seeds from which the proteinaceous material is solubilized. Alternatively, the seeds may be ground wet, using any convenient equipment, such as a high shear pump, to simultaneously grind the seed and solubilize the protein. When canola meal is utilized as the protein source, the canola meal may be any canola meal resulting from the removal of canola oil from canola oil seed with varying levels of non-denatured protein, resulting, for example, from hot hexane extraction or cold oil extrusion methods. The removal of canola oil from canola oil seed usually is effected as a separate operation from the protein product recovery procedure described herein. The proteinaceous material recovered from the canola oil seeds or canola seed meal may be the protein naturally occurring in canola seed or the proteinaceous material may be a protein modified by genetic manipulation but possessing characteristic hydrophobic and polar properties of the natural protein.

Protein solubilization from the canola protein source material is effected most conveniently using calcium chloride solution, although solutions of other calcium salts, may be used. In addition, other alkaline earth metal compounds may be used, such as magnesium salts. Further, extraction of the canola protein from the canola protein source may be effected using calcium salt solution in combination with another salt solution, such as sodium chloride. Additionally, extraction of the canola protein from the canola protein source may be effected using water or other salt solution, such as sodium chloride, with calcium salt subsequently being added to the aqueous canola protein solution produced in the extraction step. Precipitate formed upon addition of the calcium salt is removed prior to subsequent processing.

As the concentration of the calcium salt solution increases, the degree of solubilization of protein from the canola protein source initially increases until a maximum value is achieved. Any subsequent increase in salt concentration does not increase the total protein solubilized. The concentration of calcium salt solution which causes maximum protein solubilization varies depending on the salt concerned. It is usually preferred to utilize a concentration value less than about 1.0 M, and more preferably a value of about 0.10 to about 0.15 M.

In a batch process, the salt solubilization of the protein is effected at a temperature of from about 1° C. to about 100° C., preferably about 15° to about 70° C., more preferably about 20° C. to about 35° C., preferably accompanied by agitation to decrease the solubilization time, which is usually about 1 to about 60 minutes. It is preferred to effect the solubilization to extract substantially as much protein from the canola protein source as is practicable, so as to provide an overall high product yield.

In a continuous process, the extraction of the canola protein from the canola protein source is carried out in any manner consistent with effecting a continuous extraction of canola protein from the canola protein source. In one embodiment, the canola protein source is continuously mixed with the calcium salt solution and the mixture is conveyed through a pipe or conduit having a length and at a flow rate for a residence time sufficient to effect the desired extraction in accordance with the parameters described herein. In such a continuous procedure, the salt solubilization step is effected in a time of about 1 minute to about 60 minutes, preferably to effect solubilization to extract substantially as much protein from the canola protein source as is practicable. The solubilization in the continuous procedure is effected at temperatures between about 1° C. and about 100° C., preferably about 15° to about 70° C., more preferably between about 20° C. and about 35° C.

The extraction is generally conducted at a pH of about 3 to about 11, preferably about 4.5 to about 7. The pH of the extraction system (canola protein source and calcium salt solution) may be adjusted to any desired value within the range of about 3 to about 11 for use in the extraction step by the use of any convenient acid, usually hydrochloric acid or phosphoric acid, or alkali, usually sodium hydroxide, as required.

The concentration of canola protein source in the calcium salt solution during the solubilization step may vary widely. Typical concentration values are about 5 to about 15% w/v.

The protein extraction step with the aqueous salt solution has the additional effect of solubilizing fats which may be present in the canola protein source, which then results in the fats being present in the aqueous phase.

The protein solution resulting from the extraction step generally has a protein concentration of about 5 to about 50 g/L, preferably about 10 to about 50 g/L.

The aqueous calcium salt solution may contain an antioxidant. The antioxidant may be any convenient antioxidant, such as sodium sulfite or ascorbic acid. The quantity of antioxidant employed may vary from about 0.01 to about 1 wt % of the solution, preferably about 0.05 wt %. The antioxidant serves to inhibit oxidation of phenolics in the protein solution.

The aqueous phase resulting from the extraction step then may be separated from the residual canola protein source, in any convenient manner, such as by employing a decanter centrifuge or any suitable sieve, followed by disc centrifugation and/or filtration, to remove residual canola protein source material. The separated residual canola protein source may be dried for disposal. Alternatively, the separated residual canola protein source may be processed to recover some residual protein. The separated residual canola protein source may be re-extracted with fresh calcium salt solution and the protein solution yielded upon clarification combined with the initial protein solution for further processing as described below. Alternatively, the separated residual canola protein source may be processed by a conventional isoelectric precipitation procedure or any other convenient procedure to recover residual protein.

The fat present in the aqueous canola protein solution may be removed by a procedure as described in U.S. Pat. Nos. 5,844,086 and 6,005,076, assigned to the assignee hereof and the disclosures of which are incorporated herein by reference. As described therein, the aqueous canola protein solution may be chilled to a temperature of about 3° to about 7° C., to cause fat to separate from the aqueous phase for removal by any convenient procedure, such as by decanting. Alternatively, the fat may be removed at higher temperatures by centrifugation using a cream separator or defatting of the separated aqueous protein solution may be achieved by any other convenient procedure. Once the fat has been removed, the aqueous canola protein solution may be further clarified by filtration. The canola oil recovered from the aqueous canola protein solution may be processed to use in commercial applications of canola oil.

Alternatively, the aqueous canola protein solution may be simultaneously separated from the oil phase and the residual canola seed material by any convenient procedure, such as using a three phase decanter. The aqueous canola protein solution may then be further clarified by filtration.

The aqueous canola protein solution may be treated with any suitable anti-foamer, such as a food-grade, non-silicone based anti-foamer, to reduce the volume of foam formed upon further processing. The quantity of anti-foamer employed is generally greater than about 0.0003% w/v. Alternatively, the anti-foamer, in the quantity described may be added in the extraction steps.

The aqueous canola protein solution may be treated with an adsorbent, such as powdered activated carbon, granulated activated carbon or polyvinylpyrrolidone to remove colour and/or odour compounds. Such adsorbent treatment may be carried out under any convenient conditions, generally at the ambient temperature of the separated aqueous protein solution. For powdered activated carbon, an amount of about 0.025% to about 5% w/v, preferably about 0.05% to about 2% w/v, is employed. Where polyvinylpyrrolidone is used as the colour adsorbing agent, an amount of about 0.5% to about 5% w/v, preferably about 2% to about 3% w/v, may be used. The adsorbing agent may be removed from the canola protein solution by any convenient means, such as by filtration.

If of adequate purity, the resulting aqueous canola protein solution may be directly dried to produce a canola protein product. In order to provide a canola protein product having a decreased impurities content and a reduced salt content, such as a canola protein isolate, the aqueous canola protein solution may be processed as described below prior to drying.

The aqueous canola protein solution then may be concentrated to increase the protein concentration thereof while maintaining the ionic strength thereof substantially constant. Such concentration generally is effected to provide a concentrated canola protein solution having a protein concentration of at least about 50 g/L, preferably at least about 200 g/L.

The concentration step may be effected in any convenient manner consistent with batch or continuous operation, such as by employing any convenient selective membrane technique, such as ultrafiltration or diafiltration, using membranes, such as hollow-fibre membranes or spiral-wound membranes, with a suitable molecular weight cut-off (MWCO), such as about 3,000 to about 1,000,000 Daltons, preferably about 5,000 to about 100,000 Daltons, having regard to differing membrane materials and configurations and for continuous operation, dimensioned to permit the desired degree of concentration as the aqueous protein solution passes through the membranes.

As is well known, ultrafiltration and similar selective membrane techniques permit low molecular weight species to pass therethrough while preventing higher molecular weight species from so doing. The low molecular weight species include not only the ionic species of the calcium salt but also low molecular weight materials extracted from the source material, such as carbohydrates, pigments, low molecular weight proteins and anti-nutritional factors. The molecular weight cut-off of the membrane is usually chosen to ensure retention of a significant proportion of the protein in the solution, while permitting contaminants to pass through having regard to the different membrane materials and configurations.

The concentrated canola protein solution then may be subjected to a diafiltration step using water or a dilute saline solution. The diafiltration solution may be at its natural pH, at a pH equal to that of the protein solution being diafiltered or at any pH value between 3 and 11. Such diafiltration may be effected using from about 1 to about 40 volumes of diafiltration solution, preferably about 2 to about 25 volumes of diafiltration solution. In the diafiltration operation, further quantities of contaminants are removed from the concentrated canola protein solution by passage through the membrane with the permeate. The diafiltration operation may be effected until no significant further quantities of contaminants or visible colour are present in the permeate or until the retentate has been sufficiently purified so as, when dried, to provide a canola protein isolate with a protein content of at least about 90 wt % (N×6.25) d.b. Such diafiltration may be effected using the same membrane as for the concentration step. However, if desired, the diafiltration step may be effected using a separate membrane with a different molecular weight cut-off, such as a membrane having a molecular weight cut-off in the range of about 3,000 to about 1,000,000 Daltons, preferably about 5,000 to about 100,000 Daltons, having regard to different membrane materials and configuration.

Alternatively, the diafiltration step may be applied to the aqueous canola protein solution prior to concentration or to partially concentrated aqueous canola protein solution. Diafiltration may also be applied at multiple points during the concentration process. When diafiltration is applied prior to concentration or to the partially concentrated solution, the resulting diafiltered solution may then be additionally concentrated.

The concentration step and the diafiltration step may be effected herein in such a manner that the canola protein product subsequently recovered contains less than about 90 wt % protein (N×6.25) d.b., such as at least about 60 wt % protein (N×6.25) d.b. By partially concentrating and/or partially diafiltering the aqueous canola protein solution, it is possible to only partially remove contaminants. This protein solution may then be dried to provide a canola protein product with lower levels of purity.

An antioxidant may be present in the diafiltration medium during at least part of the diafiltration step. The antioxidant may be any convenient antioxidant, such as sodium sulfite or ascorbic acid. The quantity of antioxidant employed in the diafiltration medium depends on the materials employed and may vary from about 0.01 to about 1 wt %, preferably about 0.05 wt %. The antioxidant serves to inhibit the oxidation of phenolics present in the canola protein solution.

The optional concentration step and the optional diafiltration step may be effected at any convenient temperature, generally about 20 to about 60° C., preferably about 20° to about 35° C., and for the period of time to effect the desired degree of concentration and diafiltration. The temperature and other conditions used to some degree depend upon the membrane equipment used to effect the membrane processing, the desired protein concentration of the solution and the efficiency of the removal of contaminants to the permeate.

If desired, the optionally concentrated and optionally diafiltered canola protein solution may be polished by any convenient means, such as by filtering, to remove any residual particulates.

The optionally concentrated and optionally diafiltered canola protein solution may be subject to a further defatting operation, if required, as described in U.S. Pat. Nos. 5,844,086 and 6,005,076. Alternatively, defatting of the optionally concentrated and optionally diafiltered canola protein solution may be achieved by any other convenient procedure.

The optionally concentrated and optionally diafiltered canola protein solution may be subjected to an adsorbent treatment as an alternative to the adsorbent treatment described above. Powdered activated carbon may be used herein as well as granulated activated carbon (GAC) or polyvinylpyrrolidone.

The adsorbent treatment step may be carried out under any convenient conditions, generally at the ambient temperature of the optionally concentrated and optionally diafiltered canola protein solution. For powdered activated carbon, an amount of about 0.025% to about 5% w/v, preferably about 0.05% to about 2% w/v, may be used. Where polyvinylpyrrolidone is used as the colour adsorbing agent, an amount of about 0.5% to about 5% w/v, preferably about 2% to about 3% w/v, may be used. The adsorbing agent may be removed from the optionally concentrated and optionally diafiltered canola protein solution by any convenient means, such as by filtration.

The optionally concentrated and optionally diafiltered canola protein solution may be subjected to pasteurization to reduce the microbial load. Such pasteurization may be effected under any desired pasteurization conditions. Generally, the optionally concentrated and optionally diafiltered canola protein solution is heated to a temperature of about 55° to about 70° C., preferably about 60° to about 65° C., for about seconds to about 60 minutes, preferably about 10 to about 15 minutes. The pasteurized protein solution then may be cooled for further processing as described below, preferably to a temperature of about 25° to about 40° C.

The canola protein solution resulting from the optional concentration step, optional diafiltration step, optional adsorbent treatment step, optional defatting step and optional pasteurization step then may be dried by any convenient technique, such as spray drying or freeze drying, to a dry form to provide a canola protein product having a protein content of at least about 60 wt % (N×6.25) d.b., preferably a canola protein isolate having a protein content of at least about 90 wt % protein (N×6.25), preferably at least about 100 wt % protein (N×6.25).

The protein profile of the canola protein product yielded by the procedure described herein may be influenced by the processing history of the canola protein source utilized in the extraction step. Processing of the canola protein source, such as the production of canola meal from canola oil seeds, particularly with exposure of the material to elevated temperatures may reduce the quantity of protein extracted and influence the proportions of protein species extracted. Similar effects may be observed if the canola protein source is extracted at high temperatures to form the canola protein solution. The canola protein product yielded by the procedure described herein may be comprised of any proportion of 2S, 7S and/or 12S protein. Preferably the canola protein product contains fairly equal proportions of 2S and 7S, with a minor content of 12S. Such a protein profile provides a supply of essential amino acids that result in a high nutritional value for the product.

The procedure employed herein provides a canola protein product having a low phytic acid content, generally less than about 1.5 wt %, preferably less than about 0.5 wt %.

EXAMPLES

Example 1

This Example illustrates the production of the canola protein product from canola meal at pilot scale.

60 kg of canola meal was combined with 600 L of 0.15 M $CaCl_2$ solution at ambient temperature and agitated for 30 minutes to provide an aqueous protein solution. The residual solids were removed by centrifugation to produce 'a' L of centrate having a protein content of 'b' % by weight.

'c' L of centrate was reduced in volume to 'd' L by concentration on a polyethersulfone (PES) membrane, having a molecular weight cutoff of 100,000 Daltons, operated at a temperature of about 'e'° C. At this point the protein solution, with a protein content of 'f' % by weight, was diafiltered with 'g' L of RO water, with the diafiltration operation conducted at about 'h' ° C. The resulting diafiltered solution was then further concentrated at about 'i'° C. to provide 'j' kg of diafiltered, concentrated protein solution with a protein content of 'k' % by weight, which represented a yield of 'l' wt % of the initial centrate. The diafiltered, concentrated protein solution was pasteurized at 'm'° C. for 'n' minutes then dried to yield a product found to have a protein content of 'o' wt % (N×6.25) d.b. The product was termed 'p' C702.

Parameters 'a' to 'p' are detailed in Table 1 below.

TABLE 1

Parameters 'a' to 'p'

| p | SD094-C28-11A | SD094/93-E18-11A |
|---|---|---|
| a | 373.3 | 511.2 |
| b | 1.90 | 1.96 |
| c | 360 | 490 |
| d | 52 | 76 |
| e | 33 | 31 |
| f | 10.67 | n.d. |
| g | 260 | 760 |
| h | 39 | 31 |
| i | 39 | 34 |
| j | 27.7 | 38.86 |
| k | 18.85 | 18.63 |
| l | 73.6 | 72.3 |
| m | n/a | 60 |
| n | n/a | 1 |
| o | 99.40 | 99.41 | n.d. = not determined
n/a = not applicable

Example 2

This Example illustrates the production of the canola protein product from canola seed at pilot scale.

Canola seed was ground with a Commitrol and then 'a' kg of the ground seed was combined with 150 L of 0.15 M $CaCl_2$ solution at ambient temperature and agitated for 30 minutes to provide an aqueous protein solution. The residual solids were removed by centrifugation then oil was removed from the protein solution using a cream separator. The aqueous protein solution was then filtered to produce 'b' L of filtrate having a protein content of 'c' % by weight.

'd' L of filtrate was reduced in volume to 'e' L by concentration on a polyethersulfone (PES) membrane, having a molecular weight cutoff of 100,000 Daltons, operated at a temperature of about 'f'° C. At this point the protein solution, with a protein content of 'g' % by weight, was diafiltered with 'h' L of RO water, with the diafiltration operation conducted at about 'i'° C. The resulting diafiltered solution had a protein content of 'j' % by weight, which represented a yield of 'k' wt % of the initial filtrate. The diafiltered, concentrated protein solution was dried to yield a product found to have a protein content of 'l' wt % (N×6.25) d.b. The product was termed 'm' C702.

Parameters 'a' to 'm' are detailed in Table 2 below.

TABLE 2

Parameters 'a' to 'm'

| m | EC096-E24-11A | CC097-E31-11A |
|---|---|---|
| a | 22 | 22.5 |
| b | 122 | 150 |
| c | 1.06 | 1.02 |
| d | 122 | 150 |
| e | 4.5 | 5 |
| f | 29 | 30 |
| g | 17.74 | 17.12 |
| h | 45 | 50 |
| i | 31 | 31 |
| j | 11.15 | 15.10 |
| k | 41.8 | 49.3 |
| l | 100.99 | 100.57 |

Example 3

This Example illustrates the colour of the canola protein isolate powders prepared in Examples 1 and 2 as well as the colour of solutions of the canola protein isolates prepared in water.

The dry colour of the powders was determined with a HunterLab ColorQuest XE operated in reflectance mode. The results are shown in Table 3.

TABLE 3

HunterLab colour readings for C702 powders

| sample | L* | a* | b* |
|---|---|---|---|
| SD094-C28-11A C702 | 68.76 | 0.15 | 28.62 |
| SD093/94-E18-11A C702 | 71.68 | 0.22 | 27.57 |
| EC096-E24-11A C702 | 71.59 | 0.97 | 23.42 |
| CC097-E31-11A C702 | 70.34 | 1.10 | 24.10 |

As may be seen from the results in Table 3, the dry products prepared from canola seed were redder and less yellow compared to the products prepared from canola meal.

Solutions of C702 were prepared by dissolving sufficient protein powder to supply 0.48 g of protein in 15 ml of RO water. The pH of the solutions was measured with a pH meter and the colour and clarity assessed using a HunterLab Color Quest XE instrument operated in transmission mode. The results are shown in the following Table 4.

TABLE 4 pH and HunterLab scores for solutions of C702

| Sample | pH | L* | a* | b* | haze |
|---|---|---|---|---|---|
| SD094-C28-11A C702 | 4.47 | 48.92 | 11.00 | 59.15 | 94.4 |
| SD093/94-E18-11A C702 | 4.72 | 23.75 | 15.40 | 38.31 | 96.3 |
| EC096-E24-11A C702 | 5.44 | 67.88 | 6.28 | 60.29 | 93.2 |
| CC097-E31-11A C702 | 5.68 | 67.42 | 5.56 | 65.13 | 95.3 |

As may be seen from the results in Table 4, the solutions of product prepared from canola seed were higher in pH, lighter, less red and more yellow compared to the solutions of product prepared from canola meal.

Example 4

The phytic acid content of the canola protein isolates, produced by the procedures of Examples 1 and 2 were evaluated by the method of Latta and Eskin (J. Agric. Food Chem., 28: 1313-1315). The results are shown below in Table 5.

TABLE 5

Phytic acid content of C702 products

| sample | phytic acid concentration (wt %) |
|---|---|
| SD094-C28-11A C702 | 0.16 |
| SD093/94-E18-11A C702 | 0.33 |
| EC096-E24-11A C702 | 0.22 |
| CC097-E31-11A C702 | 0.26 |

As may be seen from the results in Table 5, the C702 products were very low in phytic acid.

Example 5

The protein profile of the canola protein isolates, produced by the procedures of Examples 1 and 2 was determined by HPLC size exclusion chromatography using a Phenomenex Biosep S2000 column run with a buffer of 0.05M phosphate at pH 6 containing 0.15M sodium chloride and peak detection at 280 mm.

The protein profiles of the canola protein isolates, expressed as the percentage of peak area due to each species relative to the total protein peak area, are shown in Table 6.

TABLE 6

Protein profiles of C702 products

| sample | % protein peak area 12S | % protein peak area 7S | % protein peak area 2S |
|---|---|---|---|
| SD094-C28-11A C702 | 3.0 | 62.6 | 34.4 |
| SD093/94-E18-11A C702 | 1.4 | 49.5 | 49.1 |
| EC096-E24-11A C702 | 2.9 | 58.2 | 38.9 |
| CC097-E31-11A C702 | 2.9 | 69.1 | 28.0 |

As may be seen from the results in Table 6, the C702 products contained a small amount of protein peak area due to 12S. The samples generally contained more protein peak area due to 7S than due to 2S.

Example 6

The protein solubility of the SD094-C28-11A C702 canola protein isolate, produced by the procedure of Example 1, and the CC097-E31-11A C702 canola protein isolate, produced by the procedure of Example 2 was determined using a modified version of the procedure of Morr et al, J. Food Sci. 50:1715-1718.

Sufficient protein powder to supply 0.5 g of protein was weighed into a beaker and then a small amount of reverse osmosis (RO) purified water was added and the mixture stirred until a smooth paste formed. Additional water was then added to bring the volume to approximately 45 ml. The contents of the beaker were then slowly stirred for 60 minutes using a magnetic stirrer. The pH was determined immediately after dispersing the protein and was adjusted to the appropriate level (2, 3, 4, 5, 6 or 7) with NaOH or HCl. A sample was also prepared at natural pH. For the pH adjusted samples, the pH was measured and corrected periodically during the 60 minutes stirring. After the 60 minutes of stirring, the sample was made up to 50 ml total volume with RO water, yielding a 1% w/v protein dispersion. An aliquot of the protein dispersion was reserved for protein content determination by combustion analysis using a Leco TruSpec N Nitrogen Determinator. Another portion of the sample was centrifuged at 7,800 g for 10 minutes. This sedimented any undissolved material and yielded a clear supernatant. The protein content of the supernatant was then determined by Leco analysis.

Solubility (%)=(Supernatant protein conc./Original dispersion protein conc.)×100

The natural pH of the SD094-C28-11A C702 sample was 4.50 and the natural pH of the CC097-E31-11A C702 sample was 5.70. The protein solubility results obtained are set forth in the following Table 7:

TABLE 7

Solubility of SD094-C28-11A C702 and CC097-E31-11A C702 at different pH values

| sample | pH 2 | pH 3 | pH 4 | pH 5 | pH 6 | pH 7 | Nat. pH* |
|---|---|---|---|---|---|---|---|
| SD094-C28-11A C702 | 90.9 | 91.8 | 100 | 90.9 | 87.5 | 79.8 | 95.9 |
| CC097-E31-11A C702 | 94.8 | 97.3 | 92.9 | 91.0 | 96.5 | 93.0 | 90.0 |

As may be seen from the results presented in Table 7, the protein solubility of the C702 products was high at all pH values evaluated.

Example 7

The amino acid profile of the SD094-C28-I1A C702 canola protein isolate, produced by the procedure of Example 1 was determined by three different methods to provide a complete amino acid profile and the results are shown in Table 8.

TABLE 8

Amino acid profile For SD094-C28-11A C702

| Amino acid | g/100 g amino acids |
|---|---|
| aspartic acid | 6.39 |
| threonine | 3.76 |
| serine | 3.85 |
| glutamic acid | 22.87 |
| proline | 7.80 |
| glycine | 5.32 |
| alanine | 4.37 |
| valine | 5.01 |
| isoleucine | 4.06 |
| leucine | 7.37 |
| tyrosine | 2.31 |
| phenylalanine | 4.24 |
| lysine | 5.90 |
| histidine | 3.11 |
| arginine | 6.85 |
| cystine | 2.97 |
| methionine | 2.19 |
| tryptophan | 1.61 |

SUMMARY QE THE DISCLOSURE

In summary of this disclosure, the present invention provides a procedure for the production of a canola protein product, preferably a canola protein isolate, which has a high nutritional value and a low phytic acid content. Modifications are possible within the scope of this invention.

What we claim is:
1. A method of preparing a canola protein product having a protein content of at least about 60 wt. % (N×6.25) dry weight basis (d. b.), which consists of:
  (a) extracting canola protein from canola seeds or canola oil seed meal using an aqueous calcium salt solution to provide an aqueous canola protein solution,
  (b) separating the aqueous canola protein solution from spent canola oil seed meal or residual seed material and oil if the extraction was performed on canola seeds,
  (c) concentrating the separated aqueous canola protein solution,
  (d) diafiltering the concentrated canola protein solution using water, and

(e) directly drying the canola protein solution of step (d) to provide a canola protein product having a protein content of at least about 60 wt. % (N×6.25) d.b.

2. The method of claim 1 wherein the aqueous calcium salt solution is aqueous calcium chloride solution.

3. The method of claim 1 wherein the concentration of the aqueous calcium salt solution is less than about 1.0 M.

4. The method of claim 1 wherein said extraction step is effected of a temperature of about 1° to about 100° C.

5. The method of claim 1 wherein the extraction step is effected in a pH of about 3 to about 11.

6. The method of claim 1 wherein the aqueous calcium salt solution contains an antioxidant.

7. The method of claim 6 wherein the concentration of antioxidant in the aqueous calcium salt solution is about 0.01 to about 1 wt %.

8. The method of claim 1 wherein the aqueous canola protein solution resulting from the extraction step has a protein concentration of about 5 to about 50 g/L.

9. The method of claim 1 wherein fat present in the aqueous canola protein solution after separation from residual canola protein source is at least partially removed.

10. The method of claim 1 wherein oil and residual canola source material are simultaneously removed from the aqueous canola protein solution.

11. The method of claim 1 wherein the concentration step is effected to provide a concentrated canola protein solution having a protein concentration of at least about 50 g/L.

12. The method of claim 1 wherein said concentration step is effected by ultrafiltration utilizing a membrane having a molecular weight cut-off of about 3,000 to about 1,000,000 Daltons.

13. The method of claim 1 wherein said diafiltration step is effected using about 1 to about 40 volumes of diafiltration solution optionally in the presence of an antioxidant for at least a portion of the step.

14. The method of claim 13 wherein the diafiltration step is effected using a membrane having a molecular weight cut-off of about 3,000 to about 1,000,000 Daltons.

15. The method of claim 11 or claim 13 wherein the concentration step and/or the diafiltration step are effected at a temperature of about 2° to about 60° C.

16. The method of claim 1 wherein the concentrated and diafiltered canola protein solution is dried to provide a canola protein product having a protein content of at least about 90 wt % (N×6.25).

17. The method of claim 3 wherein the concentration of the aqueous calcium salt solution is about 0.1 to about 0.15 M.

18. The method of claim 4 wherein the temperature is about 15° to about 75° C.

19. The method of claim 18 wherein the temperature is about 15° to about 35° C.

20. The method of claim 5 wherein the pH is about 4.5 to about 7.0.

21. The method of claim 7 wherein the concentration of antioxidant is about 0.05 wt %.

22. The method of claim 8, wherein the concentration of the aqueous canola protein solution is about 10 to about 50 g/L.

23. The method of claim 11 wherein the concentration of the canola protein solution is at least about 200 g/L.

24. The method of claim 12 wherein the molecular weight cut-off is about 5,000 to about 100,000 Daltons.

25. The method of claim 13, wherein the diafiltration step is effected about 2 to about 25 volumes of diafiltration solution.

26. The method of claim 14 wherein the molecular weight cut-off is about 5,000 to about 100,000 Daltons.

27. The method of claim 15 wherein the temperature is about 20° to about 35° C.

28. The method of claim 16 wherein the canola protein product having a protein content of at least about 100 wt % (N×6.25).

\* \* \* \* \*